United States Patent [19]

Rippe

[11] 4,254,097
[45] Mar. 3, 1981

[54] METHOD OF DETECTING ANTIBODIES TO HUMAN THYROGLOBULIN

[75] Inventor: Delfin F. Rippe, Miami, Fla.

[73] Assignee: American Hospital Supply Corporation, Evanston, Ill.

[21] Appl. No.: 90,954

[22] Filed: Nov. 5, 1979

Related U.S. Application Data

[62] Division of Ser. No. 911,865, Jun. 2, 1978.

[51] Int. Cl.$^3$ .................... G01N 33/52; G01N 33/68
[52] U.S. Cl. ..................................... 424/8; 23/230 B; 250/302; 424/1; 424/7; 424/12; 424/13; 435/7
[58] Field of Search ................... 424/1, 7, 8, 12, 13; 23/230 B; 435/7

[56] References Cited

U.S. PATENT DOCUMENTS 3,992,631  11/1976  Harte ................................. 424/12 X

OTHER PUBLICATIONS

Steinman, J. Clin. Invst. vol. 57, May 1976, pp. 1330–1340.
Sharp, J. Lab & Clin. Med., vol. 74, Ab. No. 160, 1969, pp. 1010–1011.
Lerman, Biochem & Biophys Acta., vol. 18, 1955, pp. 132–134.
Rothfield, J. Clin. Invst., vol. 46, 1967, pp. 1785–1794.
Tan, J. Lab. & Clin. Med., vol. 81, 1973, pp. 122–132.
Plescia, Proc. Nat. Acad. of Sci., vol. 52, No. 2, 1964, pp. 279–285.
Miles Labs Research Products Catalog C, Miles Labs. Kankakee, Ill.

*Primary Examiner*—Anna P. Fagelson
*Attorney, Agent, or Firm*—Edward A. Figg; Robert E. Hartenberger

[57] ABSTRACT

A method of detecting antibodies to native deoxyribonucleic acid (n-DNA), anti-nuclear antibodies, antibodies to non-histone containing protein, rheumatoid factors, antibodies to thyroglobulin, and an immunofluorescent assay for such detection is described. The method comprises incubating an insoluble conjugate of methylated bovine serum albumin (mBSA)-native deoxyribonucleic acid (n-DNA) or other substrates with serum from patients with systemic lupus erythematosus (SLE) or other autoimmune diseases for a sufficient length of time, washing the precipitate or flocculate, separating and discarding therefrom the supernatant fluid, adding a fluorescein labeled anti-immunoglobulin antibody to the washed flocculate and incubating the labeled mixture for a sufficient length of time, washing the incubated flocculate and separating therefrom the supernatant fluid, suspending the pellet in a liquid medium to determine the fluorescence of the flocculate, which is proportional to the concentration of antibodies to deoxyribonucleic acid and others in serum specimen. The insoluble conjugate of methylated bovine serum albumin (mBSA)-native deoxyribonucleic acid (n-DNA) retains the double-stranded form of native deoxyribonucleic acid (n-DNA).

1 Claim, No Drawings

METHOD OF DETECTING ANTIBODIES TO HUMAN THYROGLOBULIN

This is a division of application Ser. No. 911,865 filed June 2, 1978.

BACKGROUND OF THE INVENTION

This invention relates to immunofluorescent assays and more particularly, to a solid phase indirect immunofluorescent (SPIIF) assay for the detection of humoral antibodies to native deoxyribonucleic acid (n-DNA).

The use of methylated bovine serum albumin (mBSA) as a carrier for nucleic acid for purposes of immunization has been known for over a decade (Plescia et al, Proc. Nat. Acad. Sci. 52, p. 279, 1964). Methylated bovine serum albumin (mBSA) has been used also in fractionating procedures for nucleic acid purification (Mandell and Hershey, Analytical Biochemistry 1, p. 66, 1960).

The formation of deoxyribonucleic acid (DNA)-methylated bovine serum albumin conjugates was first reported Plescia et al (Proc. Nat. Acad. Sci. 52, p. 279, 1964). The primary concern of these investigators was to raise antibodies to denatured (single-stranded) DNA and to smaller polynucleotides-mBSA insoluble conjugates.

Until the present invention, there has been no use of a methylated bovine serum albumin (mBSA)-native deoxyribonucleic acid (n-DNA) precipitate (i.e., conjugate) as a substrate to detect antibodies to n-DNA. Instead, authorities have advised not to use mBSA-n-DNA conjugates for immunizations. As pointed out by Plescia et al (Proc. Nat. Sci. 52, p. 279, 1964), "The mixing of mBSA with native DNA results in the formation of a compact fibrous clot that is virtually impossible to inject."

Conventional means used to detect antibodies to native DNA include radioimmunoassays (RIA) and latex agglutination tests. However, while the former means is expensive and too time consuming; the latter is rather insensitive.

In order to overcome these disadvantages, an inexpensive, sensitive means which is not time consuming is necessary. This means is provided by the present invention as set forth and described below.

SUMMARY OF THE INVENTION

The present method of detecting and/or quantitating anti-native deoxyribonucleic acid (n-DNA) antibodies and others in serum of various specifically affected patients comprises the following steps:

A. incubating an insoluble conjugate of methylated bovine albumin (mBSA)-native deoxyribonucleic acid (n-DNA) with a serum from a patient with systemic lupus erythematosus (SLE) for a sufficient period of time;

B. washing said serum flocculate mixture and separating therefrom the supernatant fluid;

C. adding a fluorescein labeled anti-immunoglobulin antibody to the washed flocculate and incubating the labeled mixture for a sufficient period of time;

D. washing said incubated flocculate and separating therefrom the supernatant fluid; and E. suspending a pellet of the antibody mixture in a washing medium and determining the fluorescence of the flocculate, which is proportional to the concentration of said antibodies to said deoxyribonucleic acid (DNA).

According to the present invention, the anti-DNA antibodies are detected by a solid phase indirect immunofluorescent assay comprising a stable and insoluble conjugate of methylated BSA and double-stranded native deoxyribonucleic acid (n-DNA).

Other insoluble conjugates may be prepared by mixing rabbit immunoglobulin G (IgG) human thyroglobulin or a calf thymus nuclear extract (CTE) with methylated BSA. These insoluble conjugates are used as substrates for the detection of rheumatoid factors, anti-thyroglobulin antibodies and anti-nuclear antibodies, respectively, in the serum of patients suffering from autoimmune diseases.

DESCRIPTION OF PREFERRED EMBODIMENTS

The present method employs a stable, insoluble conjugate of methylated bovine serum albumin (mBSA)-native deoxyribonucleic acid (n-DNA) in solid phase indirect immunofluorescent assays for detection of antibodies to native deoxyribonucleic acid (n-DNA).

According to one embodiment of the present invention, equal amounts of the conjugate of methylated bovine serum albumin (mBSA)-native deoxyribonucleic acid (n-DNA) and the serum from a patient with systemic lupus erythematosus (SLE) are incubated for a sufficient length of time. The incubated mixture is then washed with a solution and the supernatant fluid is removed therefrom. Then, a fluorescein labeled anti-immunoglobulin antibody is added to the washed flocculate and the labeled mixture is incubated for a sufficient period of time. The incubated flocculate is then washed and the supernatant fluid is separated therefrom.

A pellet of the antibody mixture is suspended in a washing medium and the fluorescence of the flocculate is determined at 490/520 nm for excitation and the emission respectively. Since the fluorescence of the flocculate is proportional to the concentration of the antibodies to the native deoxyribonucleic acid (n-DNA), these (n-DNA) antibodies can be detected.

The incubated mixture may be washed with a washing medium such as phospate-buffered saline (PBS) containing albumin. The anti-immunoglobulin antibody (anti-immunoglobulin G or anti-immunoglobulin M) is labeled with a fluorescent agent such as fluorescein isothiocyanate.

The fluorescent values obtained for the serum from a systemic lupus erythematosus (SLE) patient are compared to a baseline fluorescent value for normal control serum. The difference in the fluorescence of the serums provides the basis for determination of the antibodies to native deoxyribonucleic acid (n-DNA) in the systemic lupus erythematosus (SLE) serum.

The assay used to detect antibodies in a serum is a solid phase indirect immunofluorescent assay comprising a stable and insoluble conjugate obtained from a soluble polymer selected from the group consisting of a double-stranded native deoxyribonucleic acid (n-DNA), rabbit immunoglobulin G (IgG) human thyroglobulin, and a calf thymus nuclear extract insolubilized with methylated bovine serum albumin (mBSA).

According to the present invention, where the soluble polymer is native deoxyribonucleic acid (n-DNA), the assay is for the detection of antibodies to native deoxyribonucleic acid (n-DNA) in systemic lupus erythematosus (SLE).

In another assay where the soluble polymer is rabbit immunoglobulin G (IgG), the assay is used to detect antibodies to immunoglobulin G (IgG) such as occurs in rheumatoid arthritis. Where the soluble polymer is human thyroglobulin, the assay is used to detect antibodies to thyroglobulin in autoimmune thyroiditis. Insolubilized calf thymus nuclear extract is used to detect anti-nuclear antibodies.

According to the present assay, other soluble materials may be used with the methylated bovine serum albumin (mBSA) to make up the insoluble conjugate for the detection of antibodies to antigens in various diseases. These soluble materials include methylated human serum albumin (mHSA) and a soluble cellular nuclear extract such as Extractable Nuclear Antigen (ENA), for the diagnosis of mixed connective-tissue disease.

In the insoluble conjugate, the methylated bovine serum albumin (mBSA) may be substituted for insolubilizing the soluble polymers (e.g., n-DNA). It has been found that when methylated human serum albumin (mHSA) is substituted for methylated bovine serum albumin (mBSA), excellent conjugates are produced. There is little difference in the detection of antibodies when methylated human serum albumin (mHSA) is used to insolubilize the soluble polymers.

The insoluble precipitate, i.e., conjugate, of methylated bovine serum albumin-native deoxyribonucleic acid (n-DNA) retains the double-stranded form of the original n-DNA as demonstrated by a fluorescent probe analysis of the precipitate, performed according to the method of Morgan and Pulleyblank (BioChem. Biophys. Res. Communications 6, 1974, p. 346).

The mBSA-n-DNA precipitate (i.e., conjugate) behaves in the assay similarly to the native deoxyribonucleic acid (n-DNA) prior to its insolubilization. That is, the conjugate retains fluorescent properties at a high pH which are characteristic of double-stranded native deoxyribonucleic acid (n-DNA).

Also, the insoluble conjugate of methylated bovine serum albumin (mBSA) or methylated human serum albumin (mHSA) and an insoluble polymer (e.g., n-DNA) retains the antigenicity of the soluble polymer. This was demonstrated by experiments in which addition of soluble DNA specifically inhibited the reactivity of lupus sera with the insoluble mBSA-DNA flocculate. Moreover, upon precipitation of mBSA with n-DNA, for example, a firm coupling is produced such that no free soluble n-DNA is detectable in the supernatant fluids after several washings. Thus, the conjugate (i.e., mBSA-n-DNA) is extremely stable.

The following examples are provided to further illustrate the preferred embodiments and advantages of the present invention.

EXAMPLE 1

Synthesis of Methylated Bovine Serum Albumin (mBSA)-Native Deoxyribonucleic Acid (n-DNA) Conjugate In accordance with the present invention, the conjugate for the detection of antibodies to native deoxyribonucleic acid was prepared as set forth below.

The native deoxyribonucleic acid (n-DNA) from calf thymus, *Escherichia coli*, or salmon sperm was dissolved in phosphate-buffered saline (PBS) at a concentration of 1.0 mg/ml. Then, methylated bovine serum albumin (mBSA) was dissolved in water at a concentration of 10 mg/ml. The two solutions were mixed at a previously established optimal ratio for maximum precipitation [700 μl of mBSA (10 mg/ml) for 1 mg n-DNA], and incubated at 37° C. for two hours.

The precipitate was washed with PBS by centrifugation until no free native deoxyribonucleic acid (n-DNA) was detected in the discarded supernatant fluid. The pellet was then suspended in PBS. The flocculate was homogenized using a glass tissue grinder to produce a more uniform suspension, and the concentration of the flocculate was standardized using a Turner 430 fluorometer at 490/520 nm (λ excitation/λ emission) and at 540/590 nm with ethidium bromide. The suspension was centrifuged and suspended in an appropriate volume of PBS supplemented with 5% BSA. The suspension was divided in 5.0 ml aliquots and lyophilized. Upon reconstitution, the suspension was tested for free (soluble) native deoxyribonucleic acid (n-DNA) by addition of ethidium bromide to the clear supernatant after centrifugation. There was no free (n-DNA) and accordingly, there was no fluorescence enhancement observed at 540/590 nm.

This insoluble conjugate was prepared for the detection of antibodies to native deoxyribonucleic acid (n-DNA) in the serum of systemic lupus erythematosus (SLE) patients.

The insoluble conjugates of rabbit immunoglobulin G (IgG)-mBSA human thyroglobulin-mBSA, and CTE-mBSA were prepared by essentially the same procedure as outlined above. The only differences were the optimal ratios of mBSA to IgG, thyroglobulin, or CTE and the addition of 0.2% gluteraldehyde for stabilization of the resultant flocculate.

EXAMPLE 2

Detection of Anti-Native Deoxyribonucleic Acid (n-DNA) Antibodies

In a borosilicate test tube, there was incubated 100 μl of methylated bovine serum albumin (mBSA)-n-DNA conjugate with 100 μl of an appropriate serum dilution (i.e., 1:2, 1:4 or 1:10) from a systemic lupus erythematosus (SLE) patient. The mixture was incubated for thirty minutes at ambient temperature. The mixture was washed by centrifugation three times with phosphate-buffered saline (PBS), i.e., 4 ml PBS was added, and the test tube was centrifuged at 2000 xg and the clear supernatant fluid aspirated.

The fluorescein labeled anti-immunoglobulin antibody was added, 100 μl of an appropriate dilution (i.e., 1:400) and incubated at ambient temperature for 30 minutes. The labeled antibody flocculate mixture was washed twice by centrifugation.

The pellet of the antibody flocculate mixture was suspended in 2.0 ml of PBS and the fluorescence was determined at 490/520 nm for excitation and emission respectively. This fluorometric assay was performed using a spectrofluorometer fitted with monochromators, i.e., the Turner 430 fluorometer.

The values obtained for the serum from systemic lupus erythematosus (SLE) patients was compared to a baseline for normal control serum.

EXAMPLE 3

Fluoroimmunoassay Tests

The fluoroimmunoassay as described above in Example 2, was used to detect the antibodies to n-DNA in the serum of systemic lupus erythematosus (SLE) patients. In order to properly detect the antibodies in the (SLE) serum, the serum of normal patients was also tested.

The following is a list of normal serum control values, each from a different individual's, along with the mean and standard deviation, which is a measure of the reproducibility of the assay. These data were obtained using the Turner 430 fluorometer. The serum was diluted 1:4.

| Fluorescence of Normal Patient Serum | |
|---|---|
| Sample Number | % F 490/520* |
| 1 | .175 |
| 2 | .180 |
| 3 | .185 |
| 4 | .185 |
| 5 | .170 |
| 6 | .175 |
| 7 | .185 |
| 8 | .175 |
| mean ± SD = .179 ± .006 | |

*The antibody used for this test was goat anti-human IgG tagged with fluorescein.

To compare with the above data, the following values are provided of the fluorescence of serum of SLE patients. The values were obtained from serum of individuals with systemic lupus erythematosus (SLE).

| Fluorescence of SLE Patient Serum | |
|---|---|
| Sample Number | % F 490/520* |
| 1 | .430 |
| 2 | .310 |
| 3 | .370 |
| 4 | .215 |
| 5 | .315 |
| 6 | .225 |
| 7 | .335 |
| 8 | .485 |

*The antibody used for this test was goat anti-human IgG tagged with fluorescein.

As shown in the above tables, there is a specific increase of fluorescence in SLE sera when compared to the baseline of normal control sera. From this experiment, it can be concluded that the serum of SLE patients have antibodies to n-DNA.

EXAMPLE 4

Specificity of Solid Phase Fluoroimmunoassay For Anti-DNA Antibodies

In order to determine whether the reaction being measured is that of DNA and anti-DNA antibodies, the following inhibition of binding experiment was performed. Serum from a patient with SLE and a normal control were divided in equal volumes of 100 μl. To each serum aliquot, 100 μl of a solution containing free DNA (ranging from 0 to 100 μg) was added and incubated for 1 hour at 37° C. Then, 100 μl of mBSA-DNA were added to each sample and the test was conducted as in Example 2.

| Serum Sample | Soluble DNA added(μg) | % F (490/520) | % Inhibition |
|---|---|---|---|
| Control | 0 | 1.08 | NA |
| | 1 | 1.08 | NA |
| | 5 | 1.10 | NA |
| | 10 | 1.10 | NA |
| | 50 | 0.88 | NA |
| | 100 | 0.84 | NA |
| SLE | 0 | 5.02 | 0 |
| | 1 | 3.62 | 35 |
| | 5 | 3.55 | 37 |
| | 10 | 3.22 | 45 |
| | 50 | 1.85 | 79 |
| | 100 | 1.58 | 86 |

NA = not applicable

Inhibition of binding SLE sera antibodies to mBSA-DNA was observed upon preicubation of the sera with soluble DNA. The degree of inhibition was proportional to the concentration of the inhibitor.

EXAMPLE 5

Comparison of Solid Phase Indirect Immunofluorescence (SPIIF) And Radioimmunoassay (RIA)

In order to compare the sensitivity of the present fluoroimmunoassay with that of radioimmunoassay (RIA), the serum from ten SLE patients was tested using the solid phase fluoroimmunoasssay (SPIIF) and a radioimmunoassay (RIA) kit distributed by Amersham/Searle. The results of the tests are provided in the table below.

The radioimmunoassay (RIA) used $I^{125}$ labeled deoxyribonucleic acid (DNA).

| Sample Number | SPIIF (% F) | RIA (% Binding) |
|---|---|---|
| 1 | 0 | 11 |
| 2 | 133 | >120 |
| 3 | 58 | 88 |
| 4 | 35 | 58 |
| 5 | 0 | 2 |
| 6 | 1 | 0 |
| 7 | 67 | 113 |
| 8 | 10 | 0 |
| 9 | >130 | >120 |
| 10 | 62 | 75 |

As shown in the table above, the SPIIF assay is as sensitive as that of the RIA assay.

EXAMPLE 6

Detection of Anti-Nuclear Antibodies Using a Calf Thymus Nuclear Extract Insolubilized with mBSA Calf thymus nuclei were purified and the nuclear material was extracted by sonication at 60 KHZ for 3 minutes in hypotonic phosphate buffer. The nuclear extract was precipitated with mBSA and washed once with a solution of 0.25% gluteraldehyde. The precipitate was used as a substrate to detect anti-nuclear antibodies using the method described in Example 2. In addition, ANA positive sera was identified using a commercially available slide kit and the antibody concentration so determined is expressed as the titer.

| Serum Samples | ANA Titer | Solid Phase Immunofluorescence | |
|---|---|---|---|
| | | Anti-γG | Anti-γM |
| Control | 0 | 0 | 0 |
| ANA + | | | |
| 1 | 1:20 | 29 | 5 |
| 2 | 1:80 | 24 | 99 |
| 3 | 1:640 | 47 | 38 |
| 4 | 1:1280 | 87 | 63 |

Anti-Nuclear antibodies of the IgG and IgM class are detectable using the solid phase fluoroimmunoassay. High titered serum samples show proportionally high fluorescence. In some instances (see 1:80 sample), the titer obtained using commercially available kits fails to reveal a prevalence of one antibody class (IgM) over another.

I claim:

1. A method for detecting antibodies to human thyroglobulin in serum comprising:

A. incubating an insoluble conjugate of methylated bovine serum albumin and human thyroglobulin with a serum from a patient for a sufficient period of time, thereby forming a serum flocculate;

B. washing said serum flocculate mixture and separating therefrom the supernatant fluid;

C. adding a fluorescein labeled anti-immunoglobulin antibody to the washed flocculate and incubating the labeled mixture for a sufficient period of time;

D. washing said incubated flocculate and separating therefrom the supernatant fluid; and E. suspending the flocculate in a washing medium and determining the fluorescence thereof, which is proportional to the concentration of antibodies to said human thyroglobulin.

* * * * *